US011426283B2

(12) United States Patent
Lefebvre et al.

(10) Patent No.: US 11,426,283 B2
(45) Date of Patent: Aug. 30, 2022

(54) MODULAR HUMERAL IMPLANT FOR AN INVERTED SHOULDER PROSTHESIS

(71) Applicant: SHOULDER FRIENDS INSTITUTE, Paris (FR)

(72) Inventors: Yves Lefebvre, Strasbourg (FR); Stephane Audebert, Blecourt (FR); Johannes Barth, Meylan (FR); Christophe Charousset, Paris (FR); Jerome Garret, Limonest (FR); David Gallinet, Geneuille (FR); Arnaud Godeneche, Saint Cyr au Mont d'Or (FR); Jacques Guery, Nevers (FR); Thierry Joudet, Libourne (FR)

(73) Assignee: SHOULDER FRIENDS INSTITUTE, Paris (FR)

( * ) Notice: Subject to any disclaimer, the term of this patent is extended or adjusted under 35 U.S.C. 154(b) by 19 days.

(21) Appl. No.: 16/885,751

(22) Filed: May 28, 2020

(65) Prior Publication Data
US 2020/0289276 A1  Sep. 17, 2020

Related U.S. Application Data

(63) Continuation of application No. PCT/FR2018/052993, filed on Nov. 27, 2018.

(51) Int. Cl.
*A61F 2/40*  (2006.01)
*A61F 2/30*  (2006.01)

(52) U.S. Cl.
CPC .......... *A61F 2/4014* (2013.01); *A61F 2/4059* (2013.01); *A61F 2/4081* (2013.01);
(Continued)

(58) Field of Classification Search
CPC ........ A61F 2/40; A61F 2/4014; A61F 2/4059; A61F 2/4081; A61F 2002/4037; A61F 2002/4077
See application file for complete search history.

(56) References Cited

U.S. PATENT DOCUMENTS 4,919,670 A * 4/1990 Dale ......................... A61F 2/40
                                                623/19.14
9,956,083 B2 * 5/2018 Humphrey ......... A61B 17/1684

FOREIGN PATENT DOCUMENTS

EP      3045149         7/2016
WO   2003039399         5/2003
(Continued)

OTHER PUBLICATIONS

International Search Report for International Application PCT/FR2018/052993, dated Apr. 16, 2019.

*Primary Examiner* — Christopher D. Prone
(74) *Attorney, Agent, or Firm* — Burris Law, PLLC

(57) ABSTRACT

A modular humeral implant for an inverted shoulder prosthesis includes a humeral stem having, on the one hand, a diaphyseal keel of elongate shape, extending along a diaphyseal axis and shaped to be engaged in a medullary cavity of a humerus, and, on the other hand, a metaphyseal portion. A humeral spacer is mounted on the metaphyseal portion of the humeral stem and has a lower face facing the metaphyseal portion, the lower face having a peripheral portion projecting laterally from the metaphyseal portion and covered at least partially with a porous or rough metal surface coating promoting an osseointegration. A humeral insert is fastened on the humeral spacer and has a hemispherical cup shaped to receive a glenosphere of a glenoid implant.

4 Claims, 5 Drawing Sheets

(52) U.S. Cl.
CPC .............. *A61F 2002/30378* (2013.01); *A61F 2002/30609* (2013.01); *A61F 2002/4037* (2013.01); *A61F 2002/4077* (2013.01); *A61F 2002/4085* (2013.01)

(56) References Cited

FOREIGN PATENT DOCUMENTS

| | | |
|---|---|---|
| WO | 2015103313 | 7/2015 |
| WO | 2017184792 | 10/2017 |

* cited by examiner

MODULAR HUMERAL IMPLANT FOR AN INVERTED SHOULDER PROSTHESIS

CROSS-REFERENCE TO RELATED APPLICATIONS

This application is a continuation of International Application No. PCT/FR2018/052993, filed on Nov. 27, 2018, which claims priority to and the benefit of FR 17/61303, filed on Nov. 28, 2017. The disclosures of the above applications are incorporated herein by reference.

FIELD

The present disclosure relates to a modular humeral implant for an inverted shoulder prosthesis.

BACKGROUND

The statements in this section merely provide background information related to the present disclosure and may not constitute prior art.

Conventionally, a humeral implant comprises:

a humeral stem having, on the one hand, a diaphyseal keel of elongate shape, extending along a diaphyseal axis and shaped to be engaged in a medullary cavity of a humerus and, on the other hand, a metaphyseal portion; and a humeral insert fastened on the metaphyseal portion and having a hemispherical cap shaped to receive a glenosphere of a glenoid implant.

Moreover, it is known to use a humeral spacer, otherwise called humeral plate, mounted on the metaphyseal portion of the humeral stem and interposed between the metaphyseal portion and the humeral insert. In other words, the humeral insert is fastened on the humeral spacer which is itself fastened on the metaphyseal portion.

The humeral spacers are generally proposed with several thicknesses and/or with several lateral offsets ("offsets") and/or with several inclinations, which allows an adaptation to the patient by offering the surgeon choices in positioning the prosthetic articular center (articulation center between the hemispherical cup of the humeral insert and the glenosphere of the glenoid implant) according to the three anatomical directions which are the anterior-posterior direction (AP), the proximal-distal direction (PD) and the medial-lateral direction (ML).

In a known manner, the humeral spacer has a lower face facing the metaphyseal portion, and this lower face has a peripheral portion projecting laterally, medially, anteriorly and posteriorly from the metaphyseal portion in order to exert a bearing on the cancellous and cortical bone cutting surface from the resection of the head of the humerus, this bearing being necessary to induce bone regeneration by compression and thus avoid a periprosthetic osteolysis.

However, wear debris from the articular friction surface of the glenosphere and/or the hemispherical cup, generally made of a polymeric material, due to the friction of the glenosphere inside the hemispherical cup, can be intrinsically interposed between this peripheral portion of the humeral spacer and the resected surface of the neck of the humerus, contributing to impair the desired bone regeneration and therefore, ultimately, to impair the anchoring of the humeral implant on the humerus.

The state of the art can be illustrated by the teaching of the document WO 2015/103313 which describes a conventional humeral implant with a humeral spacer having an upper face, a lower face and an outer peripheral face extending between the lower face and the upper face, where it is provided that a porous or rough metal surface coating covers the entire outer peripheral face, while the lower and upper faces thereof are smooth and not covered with a porous or rough metal surface coating. Although this document provides for covering the outer peripheral face with a coating promoting an osseointegration, such a humeral spacer does not provide a solution to the drawback mentioned above.

The document WO 2017/184792 mentions, in turn, a conventional humeral implant with a humeral spacer between a humeral stem and a humeral insert, where only the humeral insert is described as covered with a porous or rough metal surface coating, consequently also not providing a solution to the drawback mentioned above.

SUMMARY

This section provides a general summary of the disclosure and is not a comprehensive disclosure of its full scope or all of its features.

The present disclosure provides a solution to inhibit the insertion of such wear debris between the humeral spacer and the resected surface of the humerus head.

To this end, the present disclosure includes a modular humeral implant for an inverted shoulder prosthesis, comprising:

a humeral stem having a metaphyseal portion;

a humeral spacer mounted on the metaphyseal portion of the humeral stem and having an upper face, a lower face facing the metaphyseal portion and an outer peripheral face extending between the lower face and the upper face, said lower face having a peripheral portion projecting laterally, medially, anteriorly and/or posteriorly from the metaphyseal portion; and a humeral insert fastened on the upper face of the humeral spacer and having a hemispherical cup shaped to receive a glenosphere of a glenoid implant, wherein the humeral implant is remarkable in that the peripheral portion of the lower face of the humeral spacer is at least partially covered with a porous or rough metal surface coating promoting an osseointegration.

Thus, such a porous or rough metal surface coating will form a barrier to the wear debris from the glenosphere and/or the hemispherical cup, while promoting the osseointegration (or bone regeneration) between the humeral spacer and the cutting surface resulting from the resection of the head of the humerus.

In an advantageous form, on the humeral spacer, the porous or rough metal surface coating is provided only on the lower face, the outer peripheral face and the upper face being, in turn, smooth and not covered with a porous or rough metal surface coating.

Thus, with regard to this humeral spacer, the porous or rough metal surface coating is disposed only on the lower face with the advantages mentioned above, and on the other hand, the outer peripheral face and the upper face are smooth so as not to hinder the osseointegration at the lower face which will be used as a starting point for a rising osseointegration capable of improving the final stability.

According to one feature, the porous or rough metal surface coating is distributed on the lower face of the humeral spacer in the form of at least one ring.

In other words, the porous or rough metal surface coating is distributed on the lower face of the humeral spacer in the form of one or several ring(s).

In a first form, the porous or rough metal surface coating is distributed in the form of a single ring.

In a second form, the porous or rough metal surface coating is distributed in the form of two or more concentric rings.

According to one possibility, a pin protrudes from the lower face of the humeral spacer and forms a fitting pin shaped to be fitted inside a hole of the metaphyseal portion of the humeral stem, and the ring (or each ring) extends around the pin.

According to another possibility, the ring extends around the pin at a given distance from said pin such that the lower face has a smooth annular section between the ring and the pin, with the advantage of limiting a discomfort in the fitting of the pin into the hole of the metaphyseal portion of the humeral stem.

Advantageously, the porous or rough metal surface coating is a two-layer coating comprising a layer of porous or rough titanium or of a porous or rough titanium alloy, and a layer of calcium phosphate, such as calcium hydroxyapatite.

The present disclosure also concerns an inverted shoulder prosthesis comprising a humeral implant and further comprising a glenoid implant provided for an anchoring on a glenoid cavity and comprising a glenosphere shaped to be received inside the hemispherical cup of the humeral implant.

The present disclosure also concerns a range of humeral spacers for a modular humeral implant for an inverted shoulder prosthesis, this range comprising a plurality of humeral spacers having distinct geometric conformations, where each humeral spacer has an upper face, a lower face and an outer peripheral face extending between the lower face and the upper face, the lower face being at least partially covered with a porous or rough metal surface coating promoting an osseointegration.

Within the range, the humeral spacers can, for example, be proposed with several thicknesses and/or with several lateral offsets ("offsets") and/or with several inclinations.

Advantageously, on each humeral spacer, the porous or rough metal surface coating is provided only on the lower face, the outer peripheral face and the upper face being, in turn, smooth and not covered with a porous or rough metal surface coating.

In one particular form, the porous or rough metal surface coating is distributed on the lower face of each humeral spacer in the form of at least one ring.

According to one possibility of the present disclosure, the porous or rough metal surface coating of each humeral spacer is distributed in the form of a single ring.

According to another possibility of the present disclosure, the porous or rough metal surface coating of each humeral spacer is distributed in the form of two or more concentric rings.

According to one possibility, for each humeral spacer, a pin protrudes from the lower face and forms a fitting pin, and the ring extends around the pin.

According to another possibility, for each humeral spacer, the ring extends around the pin at a given distance from said pin such that the lower face has a smooth annular section between the ring and the pin.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

Figure 1:
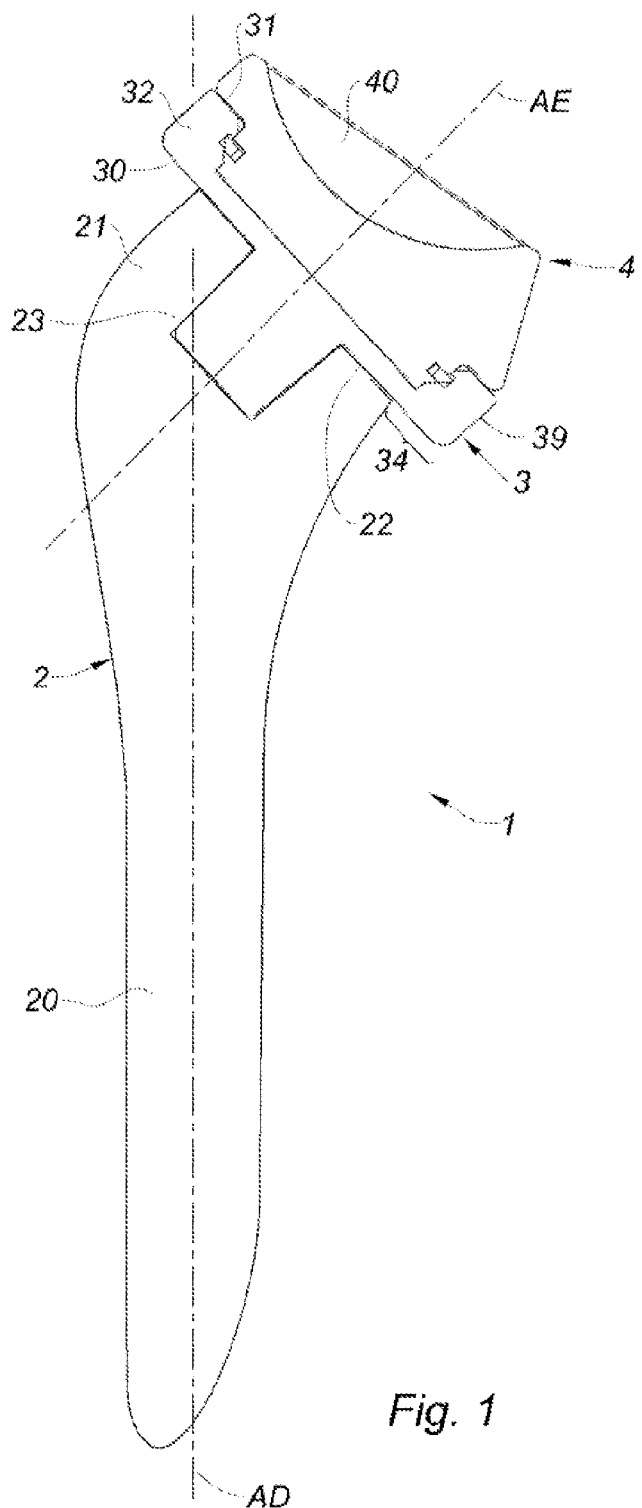
FIG. 1 is a schematic side view of a modular humeral implant according to the present disclosure.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

With reference to FIG. 1, a modular humeral implant 1 according to the present disclosure, for an inverted shoulder prosthesis (or reverse shoulder prosthesis), comprises a one-piece humeral stem 2 made of a metal material having:

a diaphyseal keel 20 of elongate shape, extends along a diaphyseal axis AD and shaped to be engaged in a medullary cavity of a humerus (not illustrated); and a metaphyseal portion 21 having a planar upper face 22 defining the bone resection plane.

A blind hole 23 is formed in the metaphyseal portion 21 by opening into the upper face 22.

The humeral implant 1 further comprises a humeral spacer 3 mounted on the upper face 22 of the metaphyseal portion 21 of the humeral stem 2, and having:

a planar lower face 30 facing the upper face 22 of the metaphyseal portion 21;

a hollow upper face 31 defining an inner cavity bordered by a peripheral wall 32; and an outer peripheral face 39 defined on the outer periphery of the peripheral wall 32 and extending between the lower face 30 and the upper face 31.

A pin 33 protrudes from the lower face 30 and forms a fitting pin shaped to be fitted inside a hole 23 of the metaphyseal portion 21 until the lower face 30 of the humeral spacer 3 abuts on the upper face 22 of the metaphyseal portion 21. This pin 33 is in the form of a Morse taper, a fitting taper, centered on a fitting axis AE.

Once the lower face 30 abuts on the upper face 22, the lower face 30 has a peripheral portion 34 projecting laterally, medially, anteriorly and posteriorly from the upper face 22 of the metaphyseal portion 21.

Figure 2:
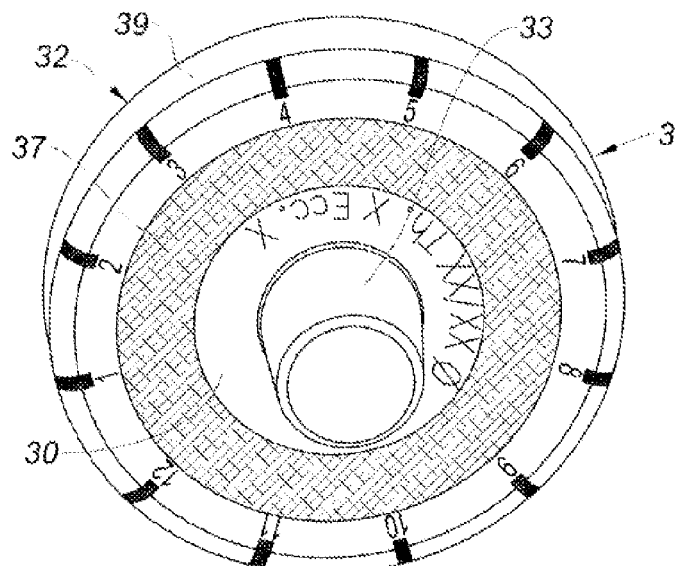
FIG. 2 is a schematic perspective bottom view of a humeral spacer for a humeral implant according to the present disclosure.
Figure 2:
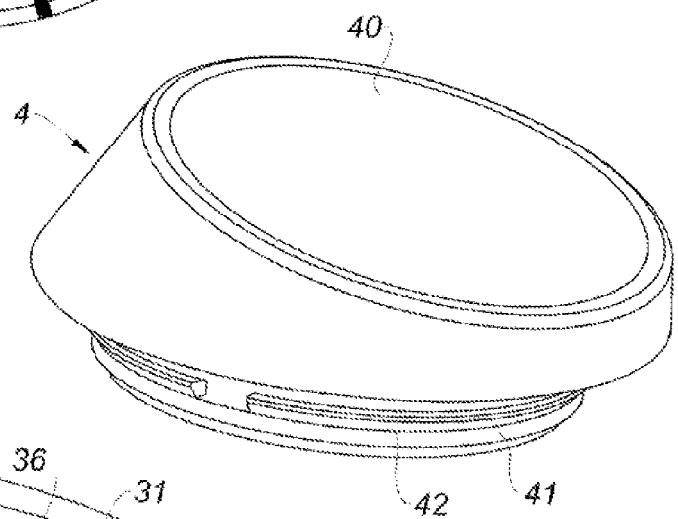

According to the present disclosure, the peripheral portion 34 of the lower face 30 is at least partially covered with a porous or rough metal surface coating 37 promoting an osseointegration. As shown in FIG. 2, this porous or rough metal surface coating 37 can be distributed on the lower face 30 of the humeral spacer 3 in the form of a ring around the pin 33. The location and the width of the porous or rough metal surface coating ring 37 will be established so that the ring at least partially covers the peripheral portion 34 around its entire perimeter.

As clearly shown in FIG. 2, it is conceivable that the ring extends around the pin 33 at a given distance from the pin 33 such that the lower face 30 has a smooth annular section between the ring and the pin 33.

Alternatively, the porous or rough metal surface coating 37 can be distributed on the lower face 30 of the humeral spacer 3 in the form of two or more concentric rings around the pin 33. In this case, it is conceivable that the smallest of the rings extends around the pin 33 at a given distance from the pin 33 such that the lower face 30 has a smooth annular section between this smallest ring and the pin 33.

The porous or rough metal coating 37 can be a two-layer coating comprising a layer of porous or rough titanium or of a porous or rough titanium alloy, and a layer of calcium phosphate, such as calcium hydroxyapatite.

Thus, the porous or rough metal surface coating 37 projects laterally, medially, anteriorly, and/or posteriorly from the upper face 22 of the metaphyseal portion 21.

Figure 6:
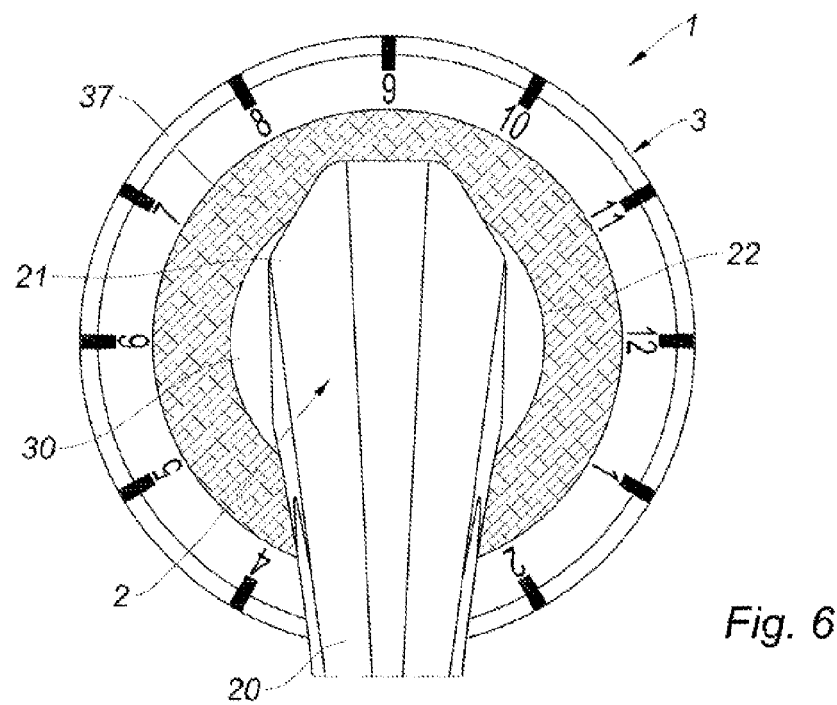
FIG. 6 is a schematic bottom view of a modular humeral implant according to the present disclosure equipped with the spacer of FIG. 2 and a first humeral stem.

In the first example illustrated in FIG. 6, the porous or rough metal surface coating 37 projects laterally, medially, anteriorly and/or posteriorly, at the same time, from the upper face 22 of the metaphyseal portion 21.

Figure 7:
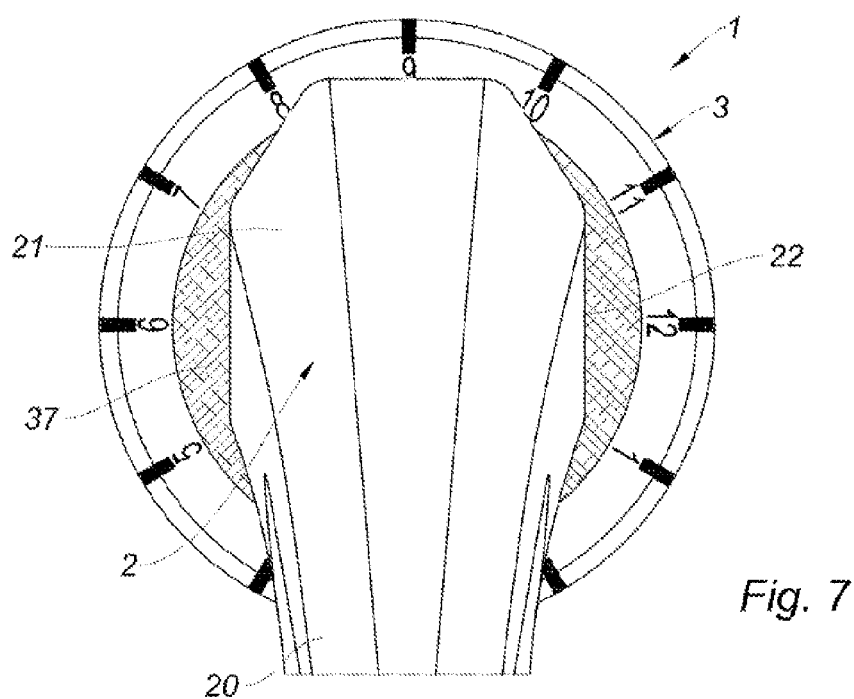
FIG. 7 is a schematic bottom view of a modular humeral implant according to the present disclosure equipped with the spacer of FIG. 2 and a second humeral stem.

In the second example illustrated in FIG. 7, the porous or rough metal surface coating 37 projects anteriorly and posteriorly from the upper face 22 of the metaphyseal portion 21.

Figure 3:
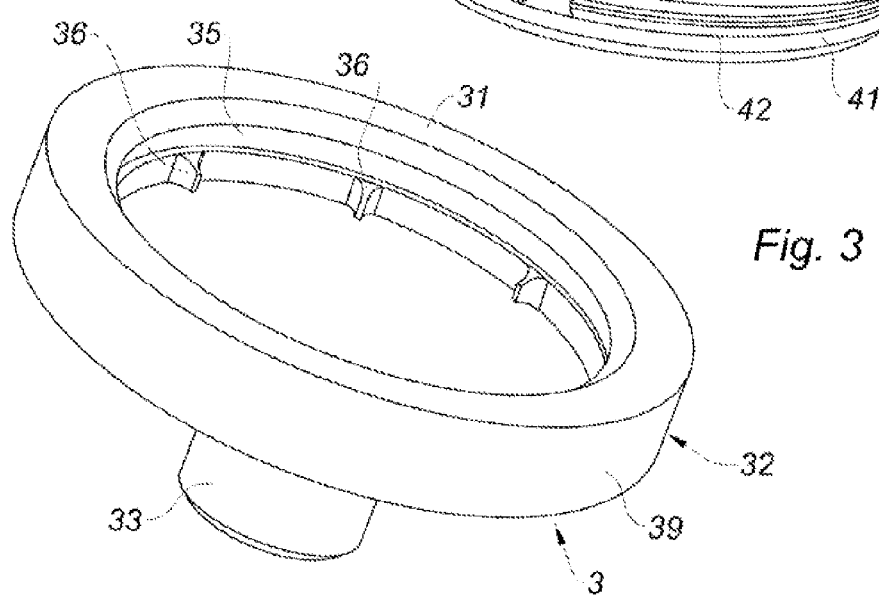
FIG. 3 is an exploded perspective view of a humeral spacer and a humeral insert before fastening for a humeral implant according to a first form of the present disclosure.

As clearly shown in FIGS. 2 and 3, on the humeral spacer 3, only the lower face 30 of the humeral spacer 3 is covered, at least partially, with such a porous or rough metal surface coating 37. In other words, the outer peripheral face 39 and also the upper face 31 of the humeral spacer 3 are not covered with a porous or rough metal surface coating, and the faces 39, 31 thereof are therefore smooth. Thus the porous or rough metal surface coating 37 is provided only on the lower face 30 of the humeral spacer 3.

The humeral spacer 3 is a metal one-piece part. The peripheral wall 32 is centered on an axis of symmetry AS.

The humeral implant 1 also comprises a humeral insert 4 fastened on the upper face 31 of the humeral spacer 3 and having a hemispherical cup 40 shaped to receive a glenosphere (not illustrated) of a glenoid implant.

Figure 4:
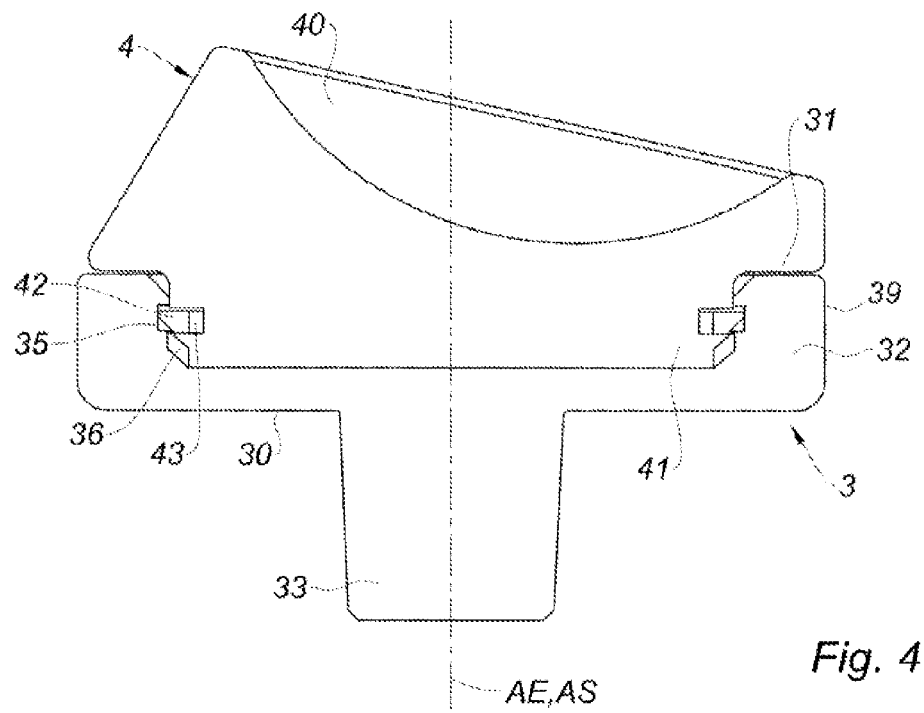
FIG. 4 is a schematic cross-sectional view of a humeral spacer and a humeral insert after fastening for a humeral implant according to the first form of the present disclosure.

In a first form illustrated in FIGS. 3 and 4, the humeral insert 4 is a one-piece part made of a polymeric or ceramic material which has a lower peripheral wall 41, overhung by the hemispherical cup 40, and on which an elastic ring 42 is provided, this elastic ring 42 being more specifically mounted in an outer groove 43 provided, for this purpose, on the peripheral wall 41. Moreover, the peripheral wall 32 of the humeral spacer 3 has an inner groove 35, below which teeth 36, which are regularly distributed over the inner perimeter of the peripheral wall 32, are provided.

Thus, in this first form, the humeral insert 4 is fastened on the upper face 31 of the humeral spacer 3 by nesting of the peripheral wall 41 inside the inner cavity of the humeral spacer 3, until engagement of the elastic ring 42 in the inner groove 35. The peripheral wall 41 also has on the edge of the notches (not shown) which are regularly distributed and designed to be engaged on the teeth 36 provided in the bottom of the cylindrical wall 32. Thus, the teeth 36 and notches provide a rotational blocking of the humeral insert 4 inside the humeral spacer 3.

Figure 5:
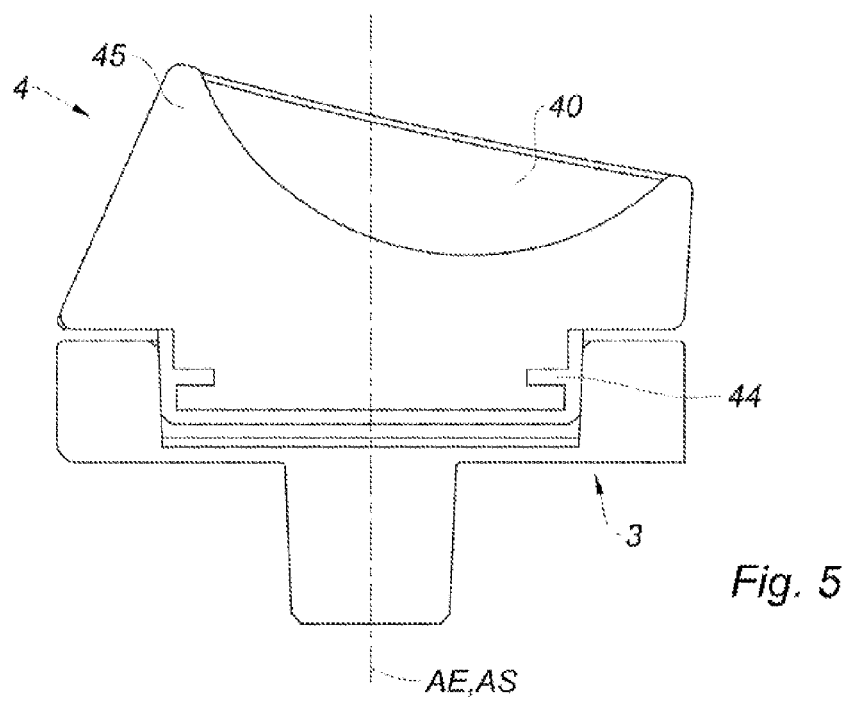
FIG. 5 is a schematic cross-sectional view of a humeral spacer and a humeral insert after fastening for a humeral implant according to a second form of the present disclosure

In a second form illustrated in FIG. 5, the humeral insert 4 is a bi-material part which comprises:
a lower frustoconical wall 44 made of a metal material and defining a male conical bearing;
an upper part 45 made of a polymeric material which is overmolded on the lower frustoconical wall 44 and having the hemispherical cup 40.

Thus, in this second form, the humeral insert 4 is fastened on the upper face 31 of the humeral spacer 3 by nesting of the lower frustoconical wall 44 inside the inner cavity defining a female conical bearing, according to a metal/metal Morse taper type mounting, in other words by a mutual wedging between the female and male conical bearings.

As shown in FIGS. 2, 6 and 7, on the lower face 30 and around the porous or rough metal surface coating 37, digital indexes positioned in an equivalent manner relative to the teeth 36 can be marked, in particular by etching, in order to allow the surgeon to visualize the rotational blocking positions of the humeral insert 4 inside the humeral spacer 3.

Figure 8:
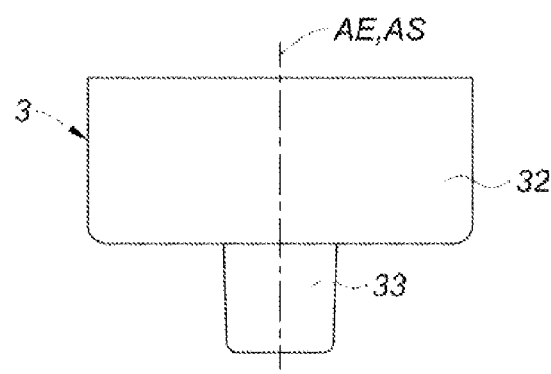
FIG. 8 is a schematic side view of a range of three humeral spacers according to the present disclosure, where the humeral spacers are distinguished by different offsets.
Figure 8:
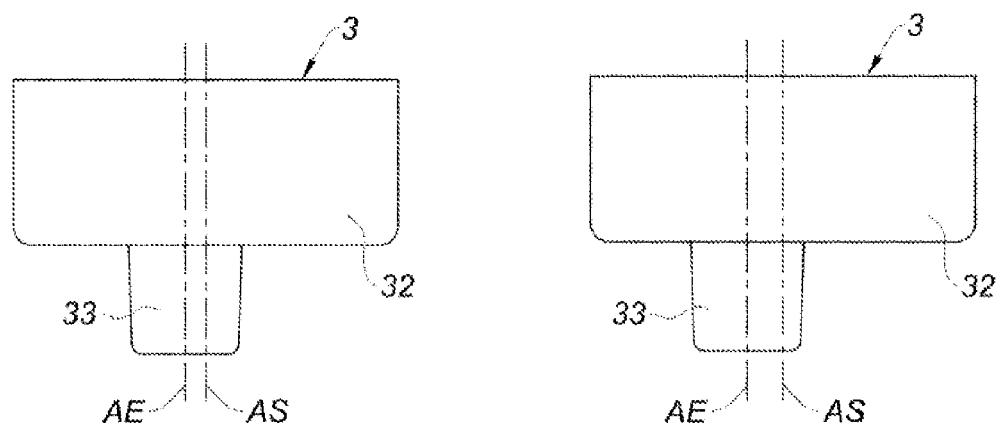

FIG. 8 illustrates a range of humeral spacers comprising a plurality of humeral spacers 3, as described above, having distinct geometric conformations. And in this example, the range includes three humeral spacer 3, where the humeral spacers 3 are distinguished by different lateral offsets; a lateral offset corresponding to a difference between the fitting axis AE and the axis of symmetry AS. The top humeral spacer 3 has a zero lateral offset, because the two axes AE and AS are combined, then the humeral spacer 3 at the bottom left has a first non-zero lateral offset DL1, for example in the range of 1 to 2 millimeters, and finally the humeral spacer 3 at the bottom right has a second lateral offset DL2 greater than DL1, for example in the range of 2 to 4 millimeters.

Unless otherwise expressly indicated herein, all numerical values indicating mechanical/thermal properties, compositional percentages, dimensions and/or tolerances, or other characteristics are to be understood as modified by the word "about" or "approximately" in describing the scope of the present disclosure. This modification is desired for various reasons including industrial practice, material, manufacturing, and assembly tolerances, and testing capability.

As used herein, the phrase at least one of A, B, and C should be construed to mean a logical (A OR B OR C), using a non-exclusive logical OR, and should not be construed to mean "at least one of A, at least one of B, and at least one of C."

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. A humeral implant for an inverted shoulder prosthesis, the humeral implant comprising:
a humeral stem having a metaphyseal portion;
a humeral spacer mounted on the metaphyseal portion of the humeral stem and having an upper face, a lower face facing the metaphyseal portion and an outer peripheral face extending between the lower face and the upper face, the lower face having a peripheral portion projecting at least one of laterally, medially, anteriorly, and posteriorly from the metaphyseal portion; and a humeral insert fastened on the upper face of the humeral spacer and having a hemispherical cup shaped to receive a glenosphere of a glenoid implant;

wherein the peripheral portion of the lower face of the humeral spacer is at least partially covered with a porous or rough metal surface coating, wherein the porous or rough metal surface coating is distributed on the lower face of the humeral spacer in a form of two or more concentric rings.

2. The humeral implant according to claim 1, wherein, on the humeral spacer, the porous or rough metal surface coating is on the lower face, and the outer peripheral face and the upper face are not covered with a porous or rough metal surface coating.

3. The humeral implant according to claim 1, wherein a pin protrudes from the lower face of the humeral spacer and forms a fitting pin shaped to be fitted inside a hole of the metaphyseal portion of the humeral stem, and the ring two or more concentric rings extend around the pin.

4. The humeral implant according to claim 3, wherein the two or more concentric rings extend around the pin at a distance from the pin such that the lower face has a smooth annular section between the two or more concentric rings and the pin.

* * * * *

UNITED STATES PATENT AND TRADEMARK OFFICE
CERTIFICATE OF CORRECTION

| | |
|---|---|
| PATENT NO. | : 11,426,283 B2 |
| APPLICATION NO. | : 16/885751 |
| DATED | : August 30, 2022 |
| INVENTOR(S) | : Yves Lefebvre et al. |

It is certified that error appears in the above-identified patent and that said Letters Patent is hereby corrected as shown below:

On the Title Page

Between item (63) and item (51), please add --(30) Foreign Application Priority Data November 28, 2017 (FR) ................17/61303.--

Signed and Sealed this
Twenty-second Day of November, 2022

Katherine Kelly Vidal
*Director of the United States Patent and Trademark Office*